US010772908B2

(12) United States Patent
Swanson

(10) Patent No.: US 10,772,908 B2
(45) Date of Patent: Sep. 15, 2020

(54) COMPOSITION FOR THE RELIEF OF DRY MOUTH

(71) Applicant: ELEVATE ORAL CARE, LLC, West Palm Beach, FL (US)

(72) Inventor: Jerome E. Swanson, St. Paul, MN (US)

(73) Assignee: ELEVATE ORAL CARE, LLC, West Palm Beach, FL (US)

(*) Notice: Subject to any disclaimer, the term of this patent is extended or adjusted under 35 U.S.C. 154(b) by 0 days.

(21) Appl. No.: 15/529,210

(22) PCT Filed: Nov. 20, 2015

(86) PCT No.: PCT/US2015/061743
§ 371 (c)(1),
(2) Date: May 24, 2017

(87) PCT Pub. No.: WO2016/094054
PCT Pub. Date: Jun. 16, 2016

(65) Prior Publication Data
US 2017/0354676 A1 Dec. 14, 2017

Related U.S. Application Data

(60) Provisional application No. 62/089,942, filed on Dec. 10, 2014.

(51) Int. Cl.
*A61K 31/78* (2006.01)
*A61K 31/047* (2006.01)
*A61K 47/10* (2017.01)
*A61K 47/26* (2006.01)
*A61K 47/32* (2006.01)
*A61K 47/38* (2006.01)
*A61K 47/54* (2017.01)
*A61K 9/00* (2006.01)
*A61K 9/06* (2006.01)
*A61K 47/40* (2006.01)

(52) U.S. Cl.
CPC .............. *A61K 31/78* (2013.01); *A61K 9/006* (2013.01); *A61K 9/06* (2013.01); *A61K 31/047* (2013.01); *A61K 47/10* (2013.01); *A61K 47/26* (2013.01); *A61K 47/32* (2013.01); *A61K 47/38* (2013.01); *A61K 47/547* (2017.08); *A61K 47/40* (2013.01)

(58) Field of Classification Search
None
See application file for complete search history.

(56) References Cited

U.S. PATENT DOCUMENTS

| 3,970,747 | A | | 7/1976 | Barth | |
|---|---|---|---|---|---|
| 4,340,583 | A | * | 7/1982 | Wason | A61Q 11/00 423/335 |
| 4,997,654 | A | * | 3/1991 | Corsello | A23G 4/10 424/440 |
| 5,496,558 | A | | 3/1996 | Napolitano et al. | |
| 5,900,230 | A | | 5/1999 | Cutler | |
| 8,658,139 | B1 | | 2/2014 | Cutler | |
| 2008/0317703 | A1 | | 12/2008 | Kawa et al. | |
| 2010/0322872 | A1 | | 12/2010 | Perraudin | |
| 2011/0028431 | A1 | | 2/2011 | Zerbe et al. | |
| 2011/0070296 | A1 | | 3/2011 | Lee et al. | |
| 2012/0053130 | A1 | * | 3/2012 | Mathias | A61K 9/0036 514/21.1 |
| 2013/0078197 | A1 | | 3/2013 | Mello et al. | |
| 2013/0209376 | A1 | | 8/2013 | Prosise et al. | |
| 2013/0272971 | A1 | | 10/2013 | Pimenta et al. | |
| 2013/0295041 | A1 | | 11/2013 | Kawa et al. | |
| 2014/0105941 | A1 | | 4/2014 | Mchale et al. | |
| 2014/0238271 | A1 | | 8/2014 | Duncan et al. | |
| 2014/0305461 | A1 | | 10/2014 | Pimenta et al. | |

FOREIGN PATENT DOCUMENTS

| JP | H03-83920 A | 4/1991 |
|---|---|---|
| JP | 2008508338 A | 3/2008 |
| JP | 2011063532 A | 3/2011 |
| WO | 2006013081 A1 | 2/2006 |
| WO | WO2012083017 A2 | 6/2012 |

OTHER PUBLICATIONS

International Search Report and Written Opinion; dated Feb. 16, 2016 for PCT Application No. PCT/US2015/061743.
Söderling, Eva M., Tiina C. Ekman, and Teemu J. Taipale. "Growth inhibition of *Streptococcus mutans* with low xylitol concentrations." Current microbiology 56.4 (2008): 382-385.
Bagul, Uddhav, et al. "In vitro study of mucoadhesive strength of polymers for mucoadhesive drug delivery systems." Int. J. Current Pharm. Res 1.1 (2009): 42-6.
Salústio, Paulo José, et al. "Advanced technologies for oral controlled release: cyclodextrins for oral controlled release." AAPS PharmSciTech 12.4 (2011): 1276-1292.
"Ashland announces availability of Lubrajel* BA hydrogel for mouth moisturization," Dec. 11, 2012, Ashland Products and Services, 2 pages.
Ashland. Innovative Ingredients for Oral Care, Brochure, 2013, pp. 1-12 as retrieved on Jan. 11, 2016 from: http://www.ashland.com/Ashland/Static/Documents/ASI/Personal%20Care/PC-12056_Oral_Care_Brochure.pdf>.
Methocel Cellulose Ethers. "Technical handbook." Midland, Michigan: Dow Chemical Company (2002), pp. title page-30.
"Spry Rain Oral Mist Spray-All Natural," Spry Dental Defense System, Xclear, 2012, 2 pages.
"Xylitol," definition in Wikipedia, the free encyclopedia, 2014, retrieved from: http://en.wikipedia.org/w/index.php?title=Xylitol&printable=yes.

(Continued)

*Primary Examiner* — Isis A Ghali
(74) *Attorney, Agent, or Firm* — Mendelsohn Dunleavy, P.C.

(57) ABSTRACT

A mucoadhesive formulation containing a clathrate host that encloses water molecules provides an effective means for, not only providing moisture to, and maintaining moisture on, a mucosal surface, but also in maintaining a high concentration of a sugar alcohol in situ on the mucosal surface for extended periods of time.

8 Claims, No Drawings

(56) References Cited

OTHER PUBLICATIONS

"Clathrate Compound," definition in Wikipedia, the free encyclopedia, 2014, retrieved from: http://en.wikipedia.org/w/index.php?oldid=605299232.
"Lubrajel BA Hydrogel Brochure," 2012, 4 pages.
European Search Report; dated Jul. 5, 2018 for EP Application No. 15867121.4.
Japanese Office Action dated Jul. 23, 2019 for the corresponding Japanese Patent Application No. 2017-550461.
"Lubrajel Series (for quasi-drugs)," Matsumoto Trading Co., Ltd., Sep. 1, 2009, Japan.
Notice of Reasons for Refusal for corresponding Japanese application No. 2017-550461; dated Feb. 4, 2020; 8 pages (Machine Translation).
Examination Report No. 1 for corresponding Australian application No. 2015361122; dated Apr. 28, 2020 (4 pages).
Communication pursuant to Article 94(3) EPC for corresponding European application No. 15867121.4; dated Mar. 3, 2020 (8 pages).

* cited by examiner

COMPOSITION FOR THE RELIEF OF DRY MOUTH

FIELD OF THE INVENTION

The present application pertains to the field of compositions for oral use to reduce discomfort related to xerostomia.

BACKGROUND OF THE INVENTION

Xerostomia, also referred to as Dry Mouth, is a chronic condition due to an inadequacy of saliva flow in the mouth. It in itself is not a disease but is a symptom associated with a wide variety of causes and conditions.

There are many causes of xerostomia, including the use of medications such as antihistamines, antidepressants, anticholinergics, anorexiants, antihypertensives, antipsychotics, anti-Parkinson agents, diuretics, sedatives, antiemetics, antianxiety agents, decongestants, analgesics, antidiarrheals, bronchodilators and skeletal muscle relaxants.

Another cause of xerostomia is as a secondary effect of a disease. The most common disease causing xerostomia is Sjögren's syndrome, a chronic inflammatory autoimmune disease. Chronic inflammatory diseases, such as sarcoidosis and amyloidosis, are also causes of xerostomia.

Systemic diseases that can cause xerostomia include rheumatoid arthritis, systemic lupus erythematosus, scleroderma, diabetes mellitus, hypertension, cystic fibrosis, bone marrow transplantation, endocrine disorders, nutritional deficiencies, nephritis, thyroid dysfunction, and neurological diseases such as Bell's palsy and cerebral palsy. Hyposecretory conditions, such as primary biliary cirrhosis, atrophic gastritis and pancreatic insufficiency, may also cause xerostomia.

Dehydration resulting from impaired water intake, emesis, diarrhea or polyuria can result in xerostomia. Psychogenic causes, such as depression, anxiety, stress or fear, can also result in xerostomia. Alzheimer's disease or stroke may alter the ability to perceive oral sensations. Dry mouth is often exacerbated by activities such as hyperventilation, breathing through the mouth, smoking, or drinking alcohol. Trauma to the head and neck area can damage the nerves supplying sensation to the mouth, impairing the normal function of the salivary glands. Additionally, xerostomia is the most common toxicity associated with radiation therapy to the head and neck.

Although xerostomia occurs in people of all ages, it is an especially common complaint in elderly people, and is estimated to affect approximately twenty percent of the elderly. In people suffering from xerostomia, common complaints secondary to the xerostomia include oral dryness when eating, the need to sip liquids in order to swallow dry foods, difficulty swallowing, and the perception of a dry mouth due to too little saliva.

Xerostomia is also responsible for secondary effects, including an increased incidence of dental caries and demineralization of teeth, and increased risk of secondary infections such as candidiasis. Therefore, ancillary treatment for xerostomia often includes the use of fluoride therapy for caries control and antifungal medications such as nystatin.

For the treatment of xerostomia itself, artificial saliva or saliva substitutes can be used to replace moisture and lubricate the mouth. These substitutes are available in a variety of formulations including solutions, sprays, gels and lozenges. These artificial saliva substitutes may contain an agent to increase viscosity, such as carboxymethylcellulose or hydroxyethylcellulose, minerals such as calcium and phosphate ions and fluoride, preservatives, and flavoring agents.

The most commonly utilized oral treatment for xerostomia is BIOTENE® (GlaxoSmithKline plc, United Kingdom). BIOTENE® is available in oral rinse and spray formulations, as well as an oral gel formulation. All formulations of BIOTENE® contain water glycerin, xylitol, and a mucoadhesive polymer. The BIOTENE® gel formulation additionally contains a carbomer as a thickening agent, in addition to its mucoadhesive properties. The sugar alcohols xylitol and sorbitol are present in the BIOTENE® formulations in small amounts in order to provide sweetness.

Kawa, U.S. Patent Application No. 2008/0317703 discloses an oral care product for xerostomia which contains a combination of polyvinyl pyrrolidone (PVP) or a vinyl pyrrolidone/vinyl acetate or vinyl alcohol copolymer in combination with an anionic mucoadhesive polymer. Kawa discloses that the anionic polymer has an affinity for mucous membranes of the oral cavity and provides good mouth coating. However, such polymers often are overly tacky and, therefore, have negative sensory characteristics. The combination of the PVP or copolymer with the mucoadhesive polymer overcomes the bad mouth feel of the composition due to the presence of the mucoadhesive polymer.

Kawa further discloses that the composition may contain additional excipients, one of which may be a humectant. If present, the humectant may be glycerin, sorbitol, xylitol, propylene glycol, polyethylene glycol, or a combination.

Soderling et al, Curr. Microbial., 56:382-385 (2008), discloses that xylitol inhibits the growth of *Streptococcus mutans*, an organism that is commonly found in the oral cavity and which is a significant contributor to the development of dental caries.

In 2012, Ashland Inc. (Covington, Ky.) announced the release of LUBRAJEL® BA for the treatment of dry mouth. LUBRAJEL® BA hydrogel is a clathrate of glycerin and polyacrylate that encloses water molecules via hydrogen bonding and Van der Waals forces. Because it binds water and is a highly viscous gel, LUBRAJEL® BA was marketed as an ingredient to provide moisture to the mouth. Ashland further disclosed that formulations containing LUBRAJEL® BA perform similarly to saliva under varying oral conditions. Moreover, these formulations had better mucoadhesion than saliva, so that it is expected that, with formulations containing LUBRAJEL® BA, the mouth will maintain longer hydration and relief from dry mouth (xerostomia).

A significant need exists for an oral care product that contains xylitol at a concentration sufficiently high to inhibit the growth of *S. mutans* and which product maintains the concentration of xylitol in the mouth, and particular on the oral mucosa, for a time sufficient for the xylitol to inhibit the growth of *S. mutans* in the mouth.

DETAILED DESCRIPTION OF THE INVENTION

It has been unexpectedly discovered that, even in the presence of a high water concentration, a mucoadhesive formulation containing a clathrate host that encloses water molecules and which is effective in holding water molecules in place on a mucosal surface is also effective in holding a sugar alcohol in place on the mucosal surface, and that the ability to hold the sugar alcohol is maintained even in the presence of high concentrations of water.

Based on this initial discovery, it has been further discovered that a mucoadhesive formulation containing a clathrate host that encloses water molecules provides an effective means for, not only providing moisture to, and maintaining moisture on, a mucosal surface, but also in maintaining a high concentration of a sugar alcohol in situ on the mucosal surface for extended periods of time. The sugar molecule is preferably xylitol and the concentration of xylitol that remains in situ may be sufficiently high in order to inhibit the development of dental caries.

Accordingly, the present application discloses, in a first embodiment, a formulation for providing moisture and the adherence of a sugar alcohol, such as xylitol, to a mucosal surface such as the oral mucosa.

The mucoadhesive formulation contains a mucoadhesive polymer. Suitable mucoadhesive polymers include cellulose polymers such as hydroxypropyl methylcellulose, hydroxypropyl cellulose, carboxymethyl cellulose, saccharide gums such as xanthan gum, guar gum, gum Arabic, and tragacanth, polyacrylic acid polymers such as carbomers or acrylate/$C_{10-30}$ alkyl acrylate cross polymers, or other polymers such as polyvinyl pyrrolidone or chitosan. In a preferred embodiment, the mucoadhesive polymer is a polyacrylic acid or polyacrylate.

The mucoadhesive polymer is present in the mucoadhesive formulation in a concentration sufficient to provide adhesion of the formulation to the oral mucosa. For example, the concentration of the mucoadhesive polymer in the formulation may be from 0.1% to 25% w/w, with a preferred range of 0.5% to 10%, and a more preferred range of 1.0% to 7%.

The mucoadhesive formulation contains a clathrate host that is capable of enclosing water. The clathrate host may be other than the mucoadhesive polymer. An example of a clathrate host that is suitable for the present invention, and which is not itself a mucoadhesive polymer, is a cyclodextrin. Examples of suitable cyclodextrins include α-cyclodextrin, β-cyclodextrin, and γ-cyclodextrin, and derivatives of cyclodextrin such as methylated cyclodextrins, ethylated cyclodextrins, hydroxypropyl cyclodextrins, and hydroxyethyl cyclodextrins.

In a preferred embodiment, the mucoadhesive polymer and the clathrate host are the same, or the mucoadhesive polymer is a component of the clathrate host. In a most preferred embodiment, the mucoadhesive polymer/clathrate host is a clathrate of glycerin and polyacrylate as sodium polyacrylate and polyacrylic acid that encloses water by hydrogen bonding and Van der Waals forces. This mucoadhesive polymer/clathrate host is marketed by Ashland Inc. (Covington, Ky.) as LUBRAJEL® BA. Additional minor components of LUBRAJEL® BA are butylene glycol, benzoic acid, and EDTA.

The mucoadhesive formulation contains water. As supplied by the manufacturer in the form of a hydrogel, LUBRAJEL® BA contains about 50% water w/w and about 50% non-water ingredients. The mucoadhesive formulation of the present application contains, in addition to the water that is provided by the LUBRAJEL® BA, a concentration of water that is at least as much as, and preferably several times higher than that of, the water concentration that is inherently in the LUBRAJEL® BA in the formulation. For purposes of this application, the water in the formulation that is not a component of the LUBRAJEL® BA in the formulation is referred to as "free water." If LUBRAJEL® BA is the clathrate host in the formulation, the free water in the formulation is the total water concentration in the formulation minus 50% of the concentration of LUBRAJEL® BA in the formulation.

As an illustrative example, the mucoadhesive formulation may contain LUBRAJEL® BA at a concentration of 10%. Of this, 50% is water and, therefore, 50% of the LUBRAJEL® BA is other than water. Therefore, the concentration of water that is inherent in a formulation containing 10% LUBRAJEL® BA is 5%. Therefore, if the concentration of free water in this example formulation is at least as high as that of the water that is a part of the LUBRAJEL® BA, the mucoadhesive formulation contains a concentration of free water of at least 5% and preferably higher than 5%.

Preferably, the concentration of free water in the mucoadhesive formulation is two or more times that of the concentration of water that is part of the LUBRAJEL® BA. In one preferred embodiment, the concentration of free water that is in the mucoadhesive formulation is 3 or more times that of the concentration of water that is part of the LUBRAJEL® BA. In a more preferred embodiment, the concentration of free water is at least 4 times, such as 5 times, 6 times, 7 times, 8 times, 9 times, 10 times, 11 times, 12 times, 13 times, 14 times, 15 times, or even more than 15 times the concentration of water that is in the LUBRAJEL® BA of the formulation.

In the formulation, the concentration of free water is between 5% and 75%. Preferably, the concentration of free water in the formulation is less than 50%, such as between 10% and 42%. As disclosed below, it is preferred that concentration of other components, such as sugar alcohols, is higher than that of free water, and may be higher than that of free water plus water that is in the LUBRAJEL® BA. That is, preferably the total amount of free water in the formulation, from all sources, and most preferably the total amount of water including free water and water that is part of the LUBRAJEL® BA, is less than 50%.

The mucoadhesive formulation contains one or more sugar alcohols of 4 to 6 carbons. Examples of sugar alcohols of 4 to 6 carbons that are suitable for the mucoadhesive formulation include 4-carbon ($C_4$) sugar alcohols such as erythritol and threitol, 5-carbon ($C_5$) sugar alcohols such as arabitol, xylitol, and ribitol, and 6-carbon ($C_6$) sugar alcohols such as nannitol, sorbitol, galactitol, fucitol, iditol, and inositol. In one preferred embodiment, the sugar alcohol is xylitol or sorbitol.

In a most preferred embodiment, the sugar alcohol is xylitol. Xylitol is preferred because, in addition to its use as a sweetener, xylitol inhibits the growth of organisms that contribute to the development of dental caries.

The concentration of the sugar alcohol in the formulation is sufficient to provide the function for which is intended. Therefore, if used as a humectant or as a sweetener, the concentration of the sugar alcohol is sufficient to provide these functions. Concentrations of sugar alcohol sufficient as a humectant or to provide sweetness to a formulation are generally between 1.0% and 10%.

In the case of xylitol, because of its anti-caries effects in addition to providing sweetness, it is preferred to have a concentration in the mucoadhesive formulation of at least 10%, so as to be capable of providing its anti-caries effect. More preferably, the concentration of xylitol in the mucoadhesive formulation is at least 15%, such as at least 20% or at least 25%. In one preferred embodiment, the concentration of xylitol in the mucoadhesive formulation is at least 30%, such as at least 35% or at least 40%. If desired, concentrations of xylitol higher than 40% may be used, such as 42%, 45%, or higher.

When the formulation contains xylitol as the sugar alcohol, it is preferred that the concentration of xylitol in the formulation be at least 25% of the concentration of the free water in the formulation. For example, the concentration of xylitol in the formulation may be at least 33% of the concentration of the free water, or at least 50% of the concentration of the free water, in the formulation. More preferably, the concentration of xylitol in the formulation is at least 75% that of the free water. Most preferably, the concentration of xylitol in the formulation is equal to or higher than that of the free water. In one particularly preferred embodiment, xylitol is the component that is in the highest concentration of all components in the mucoadhesive formulation. Thus, it is particularly preferred that the free water concentration of the formulation be less than 50% w/w.

An optional additional component of the mucoadhesive formulation is glycerin (glycerol). Glycerin is a sugar alcohol commonly used in oral preparations as a humectant. Although glycerin is a sugar alcohol, it is discussed separately in this application because it is often used in oral preparations in addition to other sugar alcohols and, unlike xylitol, glycerin is not known to have an anti-caries effect.

If present in the formulation, glycerin is at a concentration less than that of the $C_4$ to $C_6$ sugar alcohol such as xylitol. Preferably, the concentration of glycerin is less than half of the concentration of the sugar alcohol such as xylitol. More preferably, the concentration of glycerol is less than 35% that of the concentration of the sugar alcohol such as xylitol, and most preferably less than 25% that of the sugar alcohol such as xylitol.

Generally, if present, the concentration of glycerin in the formulation is less than 25%, preferably less than 20%, and most preferably less than 15%. In a most preferred embodiment, glycerin is present in a concentration less than 12%, such as 10% or less.

The mucoadhesive formulation may optionally contain other ingredients, such as flavoring agents, preservatives, buffering agents, antioxidants, decay preventing compounds such as fluorides like sodium fluoride, stannous fluoride, and sodium monofluorophosphate, and non-aqueous vehicles such as propylene glycol. Preferably, the mucoadhesive formulation is free of alcohols other than sugar alcohols.

The mucoadhesive formulation may be in any form that is useful for delivery to the oral mucosal surface, such as a liquid like a rinse or mouthspray, or as a semi-solid like a gel or a paste. Generally, similar formulations may be used as either rinse or mouthspray. Gel and paste formulations contain a thickening agent in an amount sufficient to render the formulation in the form of a semi-solid.

In another embodiment, the invention is a method for providing and preferably maintaining a sugar alcohol, such as xylitol, in situ on the oral mucosal surface and additionally providing moisture to the oral mucosal surface. In accordance with this embodiment, the mucoadhesive formulation described above in the form of a liquid, as in a rinse or mouthspray, or as a semi-solid, as in a gel or paste, is administered into the oral cavity of an individual. The formulation may be administered by any practical means, such as by rinsing, spraying, or applying into the mouth.

Preferably, the individual maintains the formulation in the oral cavity for a period of time sufficient to permit the formulation to adhere to the oral mucosa. This may be achieved by means such as gargling or by merely holding the formulation in the mouth. The time required for the formulation to adhere to the mouth may, in some cases, be instantaneous. In such situations, merely administering the formulation into the oral cavity would be sufficient for such adherence.

Because of its anti-caries effects, the sugar alcohol that is preferred for this embodiment of the invention is xylitol. Thus, as disclosed above, it is preferred that xylitol is the component that is in the highest concentration in the mucoadhesive formulation, with the possible exception of water.

An unexpected discovery concerning the administration of the mucoadhesive formulation containing xylitol as described above to the oral mucosa is the ability of the formulation to "hold" xylitol in situ on the oral mucosa at high concentrations and for extended periods of time. For example, a formulation comprising water, xylitol, and a clathrate of glycerin and polyacrylate was found to be held on the oral mucosa for several minutes in nearly identical concentration ratios as in the formulation itself. As described below in the Examples, this capability was found to be present in formulations in which the ratio in the formulation of the concentrations of free water and the water in the clathrate was more than 10 times and the concentration in the formulation of xylitol was six times that of the clathrate. This establishes that the clathrate in the formulation not only holds water, in dramatically high concentrations, but together with such high concentrations of water, simultaneously holds xylitol at high concentrations.

In another embodiment, the invention is a method for providing and retaining moisture in situ on the oral mucosal surface. In accordance with this embodiment, the mucoadhesive formulation described above in the form of a liquid, as in a rinse or mouthspray, or as a semi-solid, as in a gel or paste, is administered into the oral cavity of an individual. The formulation may be administered by any practical means, such as by rinsing, spraying, or applying into the mouth.

In accordance with this embodiment of the invention, it has been unexpectedly discovered that combining, in a formulation containing water, xylitol and a clathrate host that encloses water molecules and which is effective in holding water molecules in place on a mucosal surface provides for the holding of significantly more water than is obtained by use of the clathrate host without xylitol.

As discussed above, the clathrate host may be other than a mucoadhesive polymer, such as a cyclodextrin mentioned above, or the clathrate host may be a mucoadhesive polymer or have a mucoadhesive polymer as a component of the clathrate host. A preferred example of a clathrate host in which a mucoadhesive polymer is the clathrate host or a component of the clathrate host is a clathrate of glycerin and polyacrylate as sodium polyacrylate and polyacrylic acid that encloses water by hydrogen bonding and Van der Waals forces, such as LUBRAJEL® BA.

In accordance with this embodiment of the invention, the relative concentrations w/w % of the clathrate host, such as LUBRAJEL® BA, and xylitol are preferably between 1:1 and 1:10, with a more preferred range between 1:2 and 1:8, and a most preferred range between 1:4 and 1:6.

Preferably, the concentration of xylitol in the formulation is at least 25% of the concentration of free water in the formulation. More preferably, the concentration of xylitol is at least 50% of the concentration of free water in the formulation. Even more preferably, the concentration of xylitol is at least 75% of the concentration of free water in the formulation. In a most preferred embodiment, the concentration of xylitol in the formulation is equal to or greater than the concentration of water in the formulation.

The invention is further illustrated in the following non-limiting examples.

Example 1—Mucosal Retention of Xylitol by Prior Art Liquid Formulation

A prior art liquid formulation as disclosed in Kawa, U.S. Patent Application No. 2008/0317703, was evaluated for its ability to retain xylitol on a mucosal surface. The prior art formulation contained the following ingredients as shown in Table 1.

TABLE 1

| Ingredients | Concentration (w/w %) |
|---|---|
| Water | 52.94 |
| Glycerin | 35.00 |
| Xylitol | 7.50 |
| Vinyl pyrrolidone/vinyl acetate copolymer | 1.00 |
| PEG 60 hydrogenated castor oil | 1.60 |
| Flavor ingredients | 0.81 |
| Sodium benzoate | 0.50 |
| Xanthan gum | 0.40 |
| Methylparaben | 0.10 |
| Propylparaben | 0.10 |
| Cetylpyrindinium chloride | 0.05 |

Plastic microscope slides were coated with AVALURE™ UR 450 polymer (Lubrizol Corp., Wickliffe, Ohio), an artificial polyurethane membrane that mimics the oral mucosal surface. The coating was dried overnight at room temperature. After drying, the slides were soaked in de-ionized water for 25 minutes at which time the coating was determined to have changed from clear to slightly opaque, indicating that moisture had been absorbed.

In order to determine the percent solids in the prior art formulation, the untreated slides were weighed and then coated with the prior art formulation of Table 1 using a varnish brush. The amount of solution coated on the slides was determined by measuring weight loss from the original container. After coating, the slides were weighed and then left at a temperature of 37° C. to dry and again reweighed. After coating, the slides were weighed and then left at a temperature of 37° C. to dry and again reweighed. It was determined that the constant residual weight of the prior art formulation, that remaining after the volatile components evaporated, was 52.9%.

Plastic microscope slides were weighed and coated with the UR 450 polymer and allowed to dry. The slides were then weighed to the nearest 0.001 g. The slides were coated with the formulation of Table 1 and weighed when wet. The slides were then placed in Drip Flow Biofilm Reactor Model DFR 110 (BioSurface Technologies Corporation, Bozeman Mont.) at a 10 degree slope for one hour and exposed to a drip flow of water at a rate of 0.35 ml/min in order to mimic the flow of saliva. The slides were removed from the Reactor, allowed to dry, and were re-weighed to the nearest 0.001 g. The residual amount of wet coating was determined using the calculation of solids as described above.

After the one-hour drip flow treatment, it was determined that there was no residual coating of the prior art formulation on the slides, indicating that none of the solids, including xylitol, remained on the in-vitro oral mucosal substitute surface.

As a control, slides coated with the UR 450 polymer only were placed in the drip flow reactor and treated in the same manner as the slides coated with the prior art formulation. The weight of the slides was determined to be the same before placing in the drip flow reactor and following the one hour treatment with subsequent drying.

Example 2—Mucosal Retention of Xylitol by Liquid Formulation of the Invention

The study of Example 1 was repeated except that a liquid formulation as shown below in Table 2 was used in place of the prior art formulation of Table 1.

TABLE 2

| Ingredients | Concentration (w/w %) |
|---|---|
| Water | 40.85 |
| Glycerin | 10.00 |
| Xylitol | 42.00 |
| LUBRAJEL ® BA hydrogel | 7.00 |
| Flavor ingredients | 0.15 |

The dry weight of the liquid formulation was determined to be 45.8%, composed primarily of the xylitol and the hydrogel. The original weights of coating on the slides before drying and before drip flow treatment were 0.097 g and 0.113 g and the residual weights after treatment and subsequent drying were 0.020 g and 0.031 g, respectively.

By dividing the residual weight by the original weight multiplied by the percent dry weight, the dry weight residual percent retained on the slides was determined. This results in 45.0% and 59.9% of the formulation being retained for each sample, respectively.

This study established that the liquid formulation of the invention maintains xylitol in contact with oral mucosa for over one hour in the presence of a rate of flow of liquid that is typically found in an individual suffering from a dry mouth condition.

Example 3—Mucosal Retention of Xylitol by Prior Art Gel Formulation

The study of Example 1 was repeated except that a gel formulation of the prior art (BIOTENE® ORAL BALANCE® Dry Mouth Moisturizing Gel, GlaxoSmithKline, Philadelphia, Pa.) was used in place of the prior art liquid formulation of Table 1. The prior art gel formulation contained the following ingredients. The concentration of the ingredients was not determined. BIOTENE® ORAL BALANCE® Dry Mouth Moisturizing Gel contains glycerin, water, sorbitol, xylitol, carbomer, hydroxyethyl cellulose, sodium hydroxide, and propylparaben.

The dry weight of the prior art gel formulation was determined to be 70.1%. The original weights of coating on the slides before drying and before drip flow treatment were 0.526 g and 0.248 g and the residual weights after treatment and subsequent drying were 0.219 g and 0.077 g, respectively.

By dividing the residual weight by the original weight multiplied by the percent dry weight, the dry weight residual percent retained on the slides was determined. This results in 49% and 37% of the formulation being retained for each sample, respectively.

Example 4—Mucosal Retention of Xylitol by Gel Formulation of the Invention

The study of Example 3 was repeated except that a gel formulation as shown below in Table 3 was used in place of the prior art formulation of Example 3.

TABLE 3

| Ingredients | Concentration (w/w %) |
|---|---|
| Water | 40.35 |
| Glycerin | 5.00 |
| Xylitol | 43.00 |
| LUBRAJEL ® BA hydrogel | 10.00 |
| Carboxymethyl cellulose 7HSF | 1.50 |
| Flavor ingredients | 0.15 |

The dry weight of the gel formulation was determined to be 55.9% solids, composed primarily of the xylitol and the hydrogel. The original weights of coating on the slides before drying and before drip flow treatment were 0.150 g and 0.129 g and the residual weights after treatment and subsequent drying were 0.033 g and 0.037 g, respectively.

By dividing the residual weight by the original weight multiplied by the percent dry weight, the dry weight residual percent retained on the slides was determined. This results in 39% and 51% of the formulation being retained for each sample, respectively.

Example 5—Moisture Retention

Moisture retention was determined by applying 0.4 g of each product in a 37° C. gravity flow incubator for 2 hours and then re-weighing the amount of product remaining after that time. This test was run in a first trial comparing BIOTENE® Dry Mouth Spray (containing the ingredients shown in Table 1), SPRY RAIN with Xylitol (containing water, xylitol, aloe vera concentrate, glycerin, flavoring, calcium glycerophosphate, cellulose gum, and grapefruit seed extract as a preservative), and the liquid formulation of Example 2. This test was run in a second trial comparing BIOTENE® Dry Mouth Spray, the liquid formulation of Example 2, and a formulation similar to that of Example 2 but without xylitol (58% water, 35% glycerin, and 7% LUBRAJEL® BA hydrogel. The results are shown below in Tables 4 and 5.

TABLE 4

| TEST FORMULATION | % Moisture Loss |
|---|---|
| BIOTENE ® Dry Mouth Spray | 31.7% |
| SPRY RAIN with Xylitol | 39.5% |
| Example 2 Liquid Formulation | 18.8% |

TABLE 5

| TEST FORMULATION | % Moisture Loss |
|---|---|
| BIOTENE ® Dry Mouth Spray | 38.3% |
| Example 2 Liquid Formulation | 22.0% |
| Example 2 Liquid Formulation without xylitol | 33.5% |

The results of Tables 4 and 5 establish that the inclusion of xylitol in a formulation containing a clathrate host that encloses water, such as LUBRAJEL® BA, unexpectedly provides a dramatic increase in the moisture retention capabilities of the formulation containing the clathrate host.

While preferred embodiments of the invention have been described in detail, it will be apparent to those skilled in the art that the disclosed embodiments may be modified. It is intended that such modifications be encompassed in the invention. Therefore, the foregoing description is to be considered to be exemplary rather than limiting, and the scope of the invention is that defined by the following claims.

The invention claimed is:

1. A method for moisturizing the oral mucosa comprising applying to the oral mucosa a mucoadhesive gel or spray formulation comprising:
   10 wt. % to 50 wt. % free water,
   5 wt. % to less than 12 wt. % glycerin,
   35 wt. % to 45 wt. % xylitol,
   and a clathrate host that is capable of enclosing water, wherein the clathrate host comprises a mucoadhesive polymer which is polyacrylate; and the clathrate host is formed from glycerin and the polyacrylate,
   wherein the free water is 4 times the amount of the solids content of the clathrate host in the formulation, and the amount of the clathrate host in the formulation is sufficient to hold the xylitol in situ when the formulation is applied to oral mucosa wherein the weight percentages are based on the weight of the formulation.

2. A method for providing xylitol to the oral mucosa comprising applying to the oral mucosa a mucoadhesive gel or spray formulation comprising:
   10 wt. % to 50 wt. % free water,
   5 wt. % to less than 12 wt. % glycerin,
   35 wt. % to 45 wt. % xylitol,
   and a clathrate host that is capable of enclosing water, wherein the clathrate host comprises a mucoadhesive polymer which is polyacrylate; and the clathrate host is formed from glycerin and the polyacrylate,
   wherein the free water is 4 times the amount of the solids content of the clathrate host in the formulation, and the amount of the clathrate host in the formulation is sufficient to hold the xylitol in situ when the formulation is applied to oral mucosa wherein the weight percentages are based on the weight of the formulation.

3. The method of claim 1, wherein the xylitol is present in the formulation in a concentration of 42%-45%.

4. The method of claim 2, wherein the xylitol is present in the formulation in a concentration of 42%-45%.

5. The method of claim 1, wherein the mucoadhesive formulation is a liquid mouth spray.

6. The method of claim 2, wherein the mucoadhesive formulation is a liquid mouth spray.

7. The method of claim 1, wherein the mucoadhesive formulation is a gel.

8. The method of claim 2, wherein the mucoadhesive formulation is a gel.

* * * * *